(12) United States Patent
Robert et al.

(10) Patent No.: US 7,838,836 B2
(45) Date of Patent: Nov. 23, 2010

(54) METHOD FOR DETECTING A SPRAY OF WATER AT THE REAR OF A VEHICLE

(75) Inventors: Caroline Robert, Paris (FR); Joël Leleve, Epinay sur Seine (FR); David Hue, Chatou (FR)

(73) Assignee: Valeo Vision, Bobigny (FR)

( * ) Notice: Subject to any disclaimer, the term of this patent is extended or adjusted under 35 U.S.C. 154(b) by 116 days.

(21) Appl. No.: 12/181,564

(22) Filed: Jul. 29, 2008

(65) Prior Publication Data

US 2009/0032712 A1 Feb. 5, 2009

(30) Foreign Application Priority Data

Aug. 3, 2007 (FR) .................................. 07 05713

(51) Int. Cl.
*G01J 5/02* (2006.01)

(52) U.S. Cl. .................................................. 250/341.7

(58) Field of Classification Search ............... 250/341.7
See application file for complete search history.

(56) References Cited

U.S. PATENT DOCUMENTS

| | | | |
|---|---|---|---|
| 3,901,812 A | | 8/1975 | Hallengren |
| 4,274,091 A | * | 6/1981 | Decker ........................ 340/583 |
| 4,928,015 A | * | 5/1990 | Butler et al. ................. 250/343 |
| 4,931,767 A | | 6/1990 | Albrecht et al. |
| 2004/0239923 A1 | * | 12/2004 | Adams et al. ................ 356/317 |
| 2005/0180149 A1 | * | 8/2005 | Albou et al. ................. 362/459 |
| 2007/0007449 A1 | * | 1/2007 | Hubner et al. ............ 250/338.1 |
| 2008/0165031 A1 | * | 7/2008 | Estrada et al. .............. 340/963 |

FOREIGN PATENT DOCUMENTS

| | | |
|---|---|---|
| DE | 19620147 A1 | 12/1996 |
| DE | 19749397 A1 | 5/1998 |
| DE | 102005054497 A1 | 5/2007 |
| EP | 1604865 A1 | 12/2005 |
| FR | 2560353 A1 | 8/1985 |

\* cited by examiner

*Primary Examiner*—David P Porta
*Assistant Examiner*—Kiho Kim
(74) *Attorney, Agent, or Firm*—Jacox, Meckstroth & Jenkins

(57) ABSTRACT

A method for detecting a phenomenon affecting visibility generated by an automotive vehicle, comprising the steps of emitting a first beam of light, which beam of light can be reflected by an obstacle; emitting a second reference beam of light using a second emitting source; receiving on a receiver the reflected beam of light resulting from the first beam of light being reflected by an obstacle, and the second beam of light sent directly to the input of the receiver; generating one or more detection signals as a function of a combination of the reflected beam of light in the event of an obstacle and a reference beam; and comparing the modulation of one or more detection signals generated using reference data. According to the invention, the first and second beams of light are infra-red beams, and they are directed towards the rear of the vehicle.

18 Claims, 5 Drawing Sheets

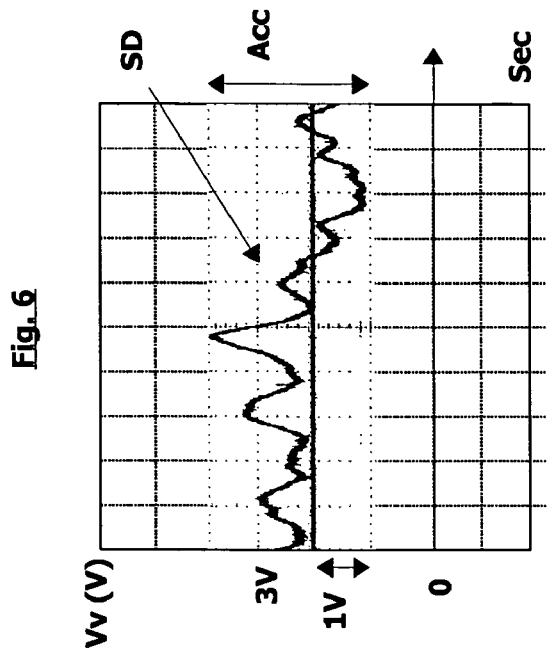
Fig. 6
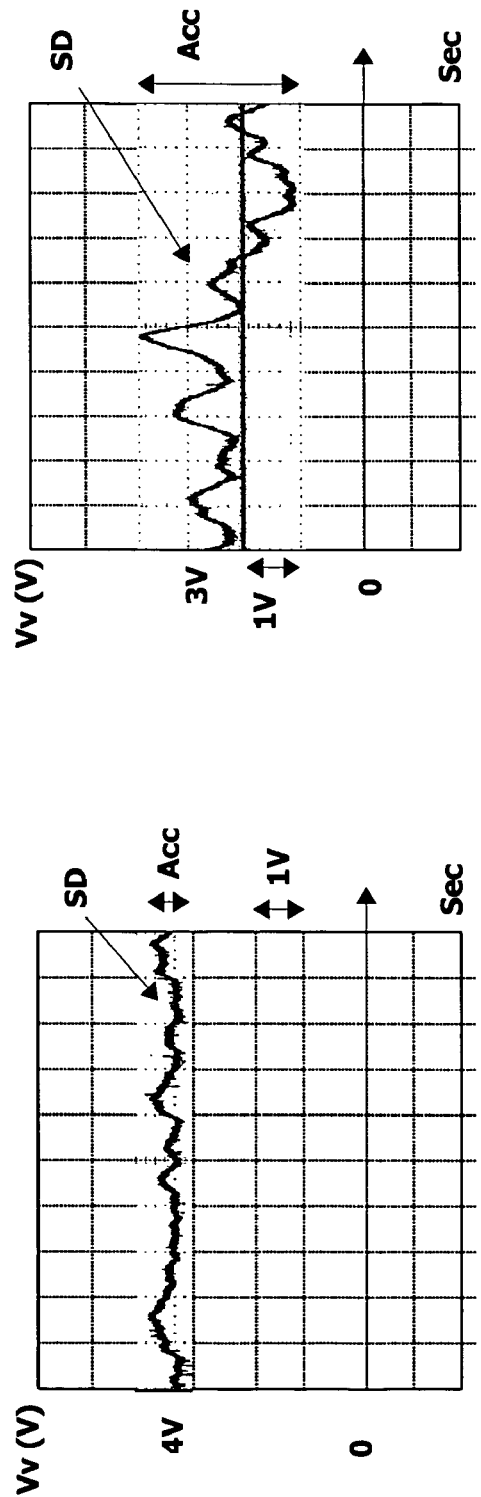
Fig. 7
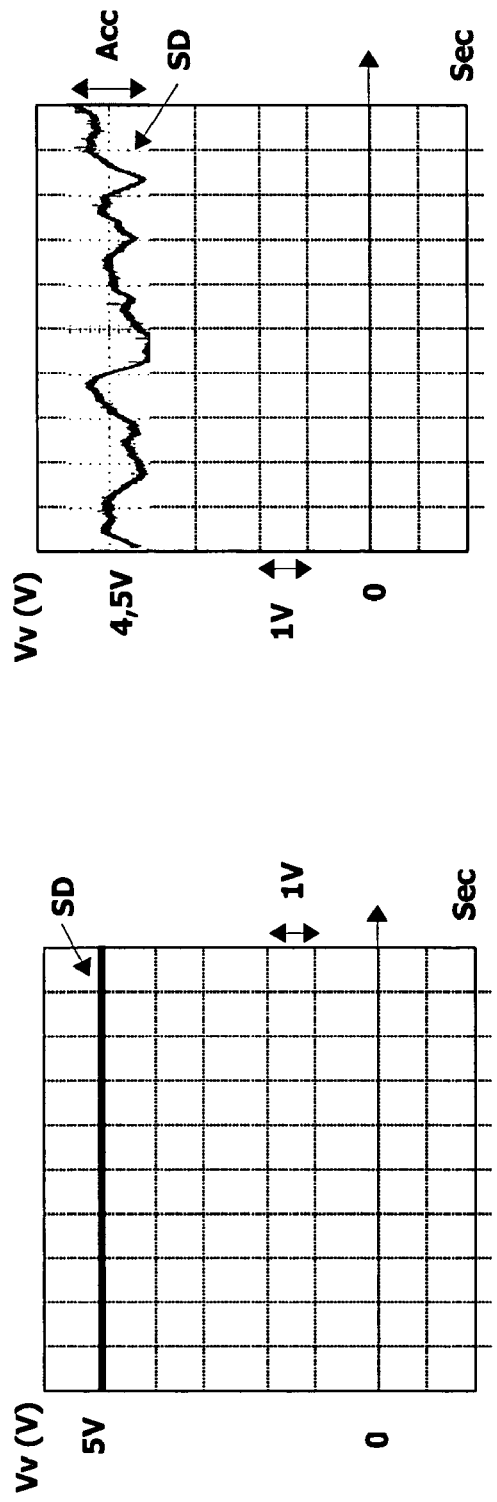
Fig. 4
Fig. 5

METHOD FOR DETECTING A SPRAY OF WATER AT THE REAR OF A VEHICLE

CROSS-REFERENCE TO RELATED APPLICATIONS

This application claims priority to French Application No. 0705713 filed Aug. 3, 2007, which application is incorporated herein by reference and made a part hereof.

BACKGROUND OF THE INVENTION

1. Field of the Invention

The present invention concerns a method for detecting phenomena affecting visibility generated by an automotive vehicle, and a detection device enabling the method to be used.

It finds a particular application in the field of automotive vehicles.

2. Description of the Related Art

As applied in automotive vehicles, methods for detecting solid obstacles such as a following vehicle are known from the state of the art, making it possible for example to warn if the following vehicle is getting too close. They do this by using a variety of sensors such as a radar, a LIDAR or a rear vision camera. If such an obstacle exists, and the rear lights are on, if the road is wet (whether it is raining or not), the visibility of the lights may be affected by a phenomenon affecting visibility, such as a spray of water generated by the vehicle's rear wheels, for the driver of the following vehicle, which may make that following driver unsure to some extent. Such methods cannot be used to detect such phenomena affecting visibility.

SUMMARY OF THE INVENTION

The purpose of the present invention is to make it possible to detect a phenomenon affecting visibility generated by an automotive vehicle.

According to a first object of the invention, this aim is achieved by a method for detecting a phenomenon affecting visibility generated by an automotive vehicle, comprising steps as follows:

emitting a first beam of light, which can be reflected by an obstacle;

emitting a second reference beam of light from a second source;

using a receiver to receive the reflected beam of light resulting from the first beam of light being reflected from an obstacle, and the second beam of light sent directly to the receiver's input;

generating one or more detection signals as a function of a combination of the reflected beam of light and a reference beam; and comparing the modulation of one or more detection signals generated using reference data.

According to the invention, the first and second beams of light are infra-red beams, and are directed towards the rear of the vehicle.

As will be seen in detail from what follows, such a method has the advantage that it is based on a detection signal which presents a characteristic modulation of a phenomenon affecting visibility such as a spray of water and hence determine that such a phenomenon is present.

According to non-limitative embodiments, the method also shows the characteristics as follows:

the combination is composed of a summing of the two beams, a phase shift and an amplitude shift of these two beams. This makes it possible to obtain two detection signals easily;

one detection signal corresponds to a phase shift between the reflected beam of light and the reference beam. This detection signal can be used in particular to determine a distance between an obstacle and the rear of the vehicle;

the reference data is a preset modulation threshold. Thanks to this modulation threshold, it is possible to tell the difference between the presence of a spray of water which affects visibility and the absence of a spray of water, in a dry or humid atmosphere which does not, however, affect visibility;

the reference data is an amplitude moderation threshold. This data is easy to compare, as the amplitude moderation of a detection signal can be read off directly from the signal itself without any particular prior processing being required;

the beam of light is emitted starting from a preset speed threshold of the vehicle. Below that threshold, in fact, no spray of water is generated, or, if it is generated, it is not disturbing at low speed; and the phenomenon affecting visibility consists of a spray of water generated by the vehicle's wheels.

According to a second object of the invention, it concerns a device for detecting a phenomenon affecting visibility generated by an automotive vehicle, comprising:

a first emitting source, for emitting a beam of light to light the rear of the vehicle, that beam of light being capable of being reflected by an obstacle;

a second emitting light source emitting a reference beam of light;

a receiver to receive:
 the reflected beam of light resulting from the beam of light being reflected off an obstacle; and
 the reference beam of light sent directly to its input; and a control unit for:
 generating one or more detection signals as a function of a combination of the reflected beam of light if there is an obstacle and a reference beam; and
 comparing the modulation of one or more detection signals generated using reference data.

According to this second object of the invention, the first and second beams of light are infra-red beams, and are directed towards the rear of the vehicle.

In a non-limitative embodiment, the detection device is activated from a preset speed threshold of the vehicle. Below this threshold, in fact, no spray of water is generated, or, if it is generated, it is not a nuisance at low speed. This also makes it possible to consume less current.

According to a third object of the invention, it concerns a computer software product comprising one or more sequences of instructions which can be executed by a data processing unit, executing the sequences of instructions enabling the method to be implemented as in any of the characteristics above.

These and other objects and advantages of the invention will be apparent from the following description, the accompanying drawings and the appended claims.

BRIEF DESCRIPTION OF THE ACCOMPANYING DRAWINGS

Other characteristics and advantages of the present invention will be better understood with the aid of the specification and non-limitative drawings, amongst which:

FIG. 4 is a plot of a detection signal produced by the method as in FIG. 1, the detection signal being representative of the absence of any phenomena affecting visibility and the presence of a solid obstacle;

FIG. 5 is a plot of a detection signal produced by the method as in FIG. 1, the detection signal being representative of the absence of any phenomena affecting visibility and the presence of a solid obstacle;

FIG. 6 is a plot of a detection signal produced by the method as in FIG. 1, the detection signal being representative of the presence of a phenomenon affecting visibility and the absence of a solid obstacle;

FIG. 7 is a plot of a detection signal produced by the method as in FIG. 1, the detection signal being representative of the presence of a phenomenon affecting visibility and the presence of a solid obstacle.

DETAILED DESCRIPTION OF THE PREFERRED EMBODIMENTS

If a road is wet, the turbulence created at the rear of an automotive vehicle, such as a car, truck etc. (when it is moving) are the mingling of a number of sprays of water (this is not a smooth phenomenon). This may make its rear lights less visible to the driver of a following vehicle. There is then an interest in making the rear lights stronger to make them more visible and thereby to detect the presence of these sprays of water at the rear of the vehicle beforehand.

The method and device described herein as in the invention can be used to detect a phenomenon affecting the visibility of a vehicle's rear lights such as a spray of water. It is described in a non-limitative embodiment in FIG. 1.

Figure 1:
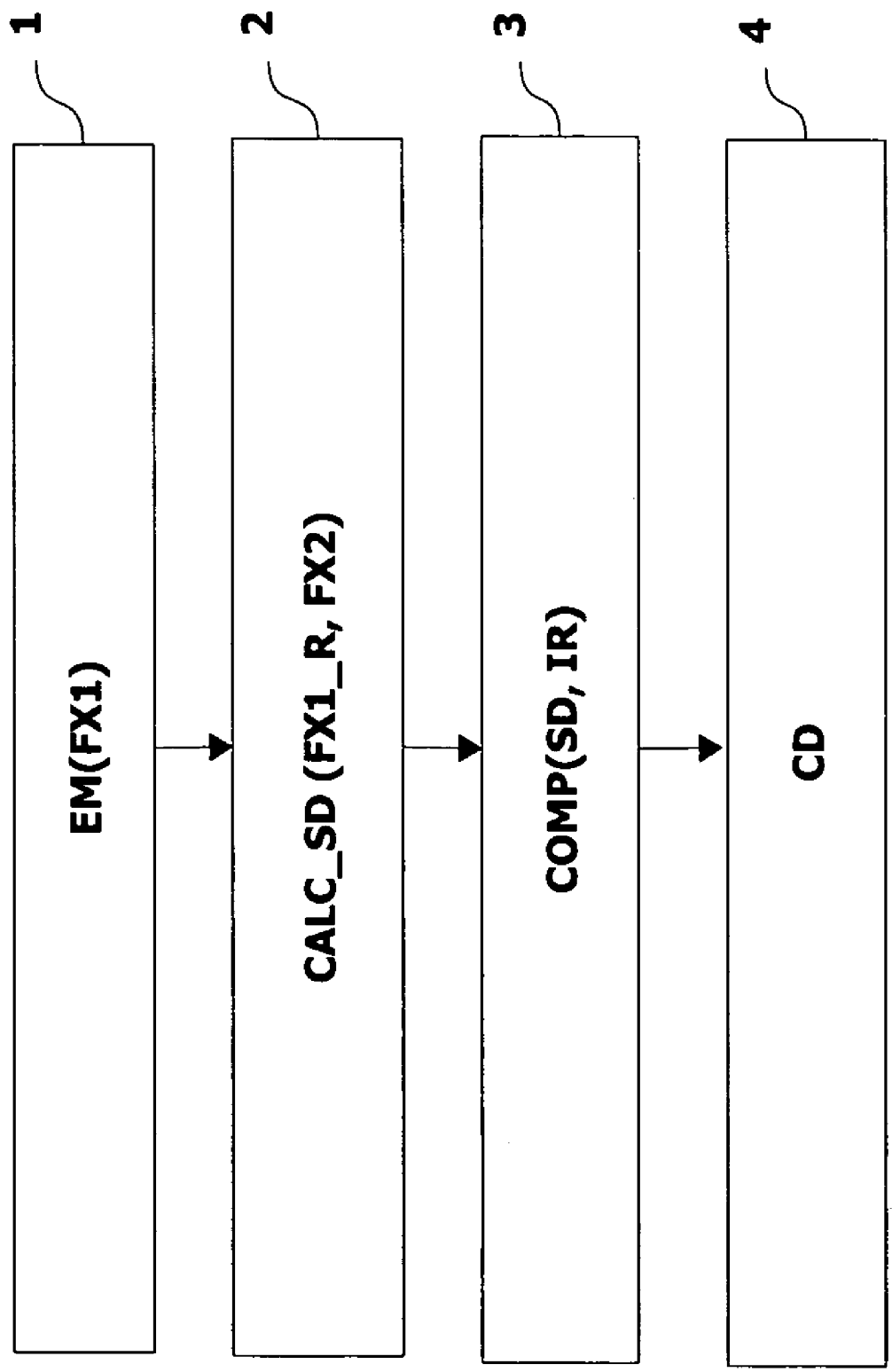
FIG. 1 represents a diagram of a non-limitative embodiment of the detection method as in the invention.

The detection method comprises a number of steps, as shown in FIG. 1:
  emitting a beam of light FX1 to light the rear of the vehicle (step EM (FX1) as shown in FIG. 1), the beam of light being capable of being reflected by an obstacle O;
  generating one or more detection signals SD as a function of a combination of the reflected beam of light FX1_R in the event of an obstacle O and a reference beam FX2 (step CALC_SD (FX1_R, FX2) as shown in FIG. 1); and
  comparing the modulation of one or more generated detection signals SD with reference data IR (step COMP (SD, IR) as shown in FIG. 1).

The steps are described in detail below.

In a first step (1), a beam of light FX1 is emitted to illuminate the rear of vehicle V1, the beam of light being capable of being reflected by an obstacle O at the rear of vehicle V1.

An obstacle O (behind vehicle V1) may be:
  a "solid" obstacle, such as a following vehicle V2; or
  a "non-solid" or "soft" obstacle, such as a spray of water G1 created by the wheels of vehicle V1; or
  a combination of a "solid" obstacle and a "soft" obstacle, such as a following vehicle V2 and a spray of water G1 created because the road is wet.

It will be noted that a spray of water is composed of a number of drops of water.

In a non-limitative embodiment, the emitted beam of light FX1 is an infra-red beam with a wavelength close to 850 nm. This avoids creating unwanted light effects on the rear of the vehicle if a nuisance phenomenon G1 arises, causing a nuisance to following drivers.

In a non-limitative embodiment, moreover, beam FX1 is narrow. In a non-limitative embodiment, it has a spread of 4°, which avoids it losing power. This concentrates the energy in the beam of light FX1 and makes it possible to detect interfering phenomena at greater distances.

Beam of light FX1 is generated by a light source SRC1 integrated in a sensor CAPT. The source and sensor are described further on.

In a first non-limitative limitation, beam of light FX1 is generated when the rear lights come on: so it remains on all the time those lights are on. This makes it certain that an interfering phenomenon can be detected, such as a spray of water when it rains or when the road is wet and to increase the brightness of the rear lights accordingly.

In a second embodiment, beam of light FX1 is generated from a preset speed threshold SV of the vehicle V. In a non-limitative example, this threshold SV is set at 50 km/h. In fact, as no spray of water will be generated below a certain speed, this means the beam of light can be made to work when there is a spray of water or if the presence of that spray becomes a nuisance (it is not a nuisance to a following driver at low speed). This second mode is thus more economic and certain than the first mode, as it avoids unwanted lights in the eye of the following vehicle V2.

The first and second embodiments may be combined, of course.

Beam FX1 thus emitted is reflected by any solid obstacle (vehicle, wall, pedestrian, etc. . . . ) and/or "soft" one (water, fog etc. . . . ) at the rear of vehicle V1, and the reflected beam FX1_R which results returns from the direction of the emitting source SRC1 and is perceived by a receiver RCV. This reflected beam FX1_R is deformed by the obstacle, putting it out of phase relative to emitted beam FX1.

Figure 2:
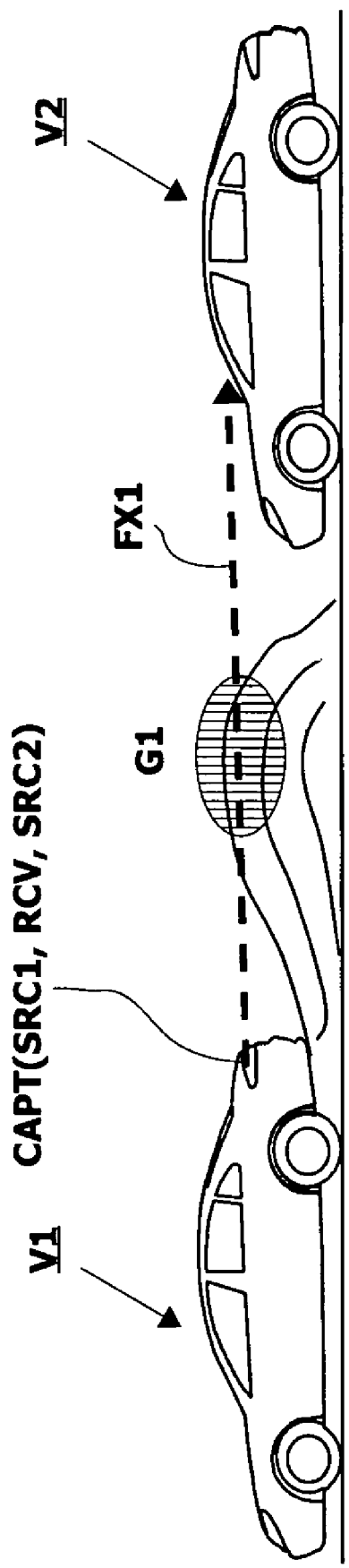
FIG. 2 is a schematic representation of a vehicle generating a phenomenon affecting visibility detected by the method as in FIG. 1.

FIG. 2 shows an example of a beam of light FX1 emitted by a first light source SRC1 from a vehicle V1 which is reflected by a "soft" obstacle, in this case a spray of water G1 created by the rear wheels of vehicle V1, and by a "solid" obstacle, in this case following vehicle V2. The reflection of beam FX1 in the water is also known as back scatter.

Figure 3:
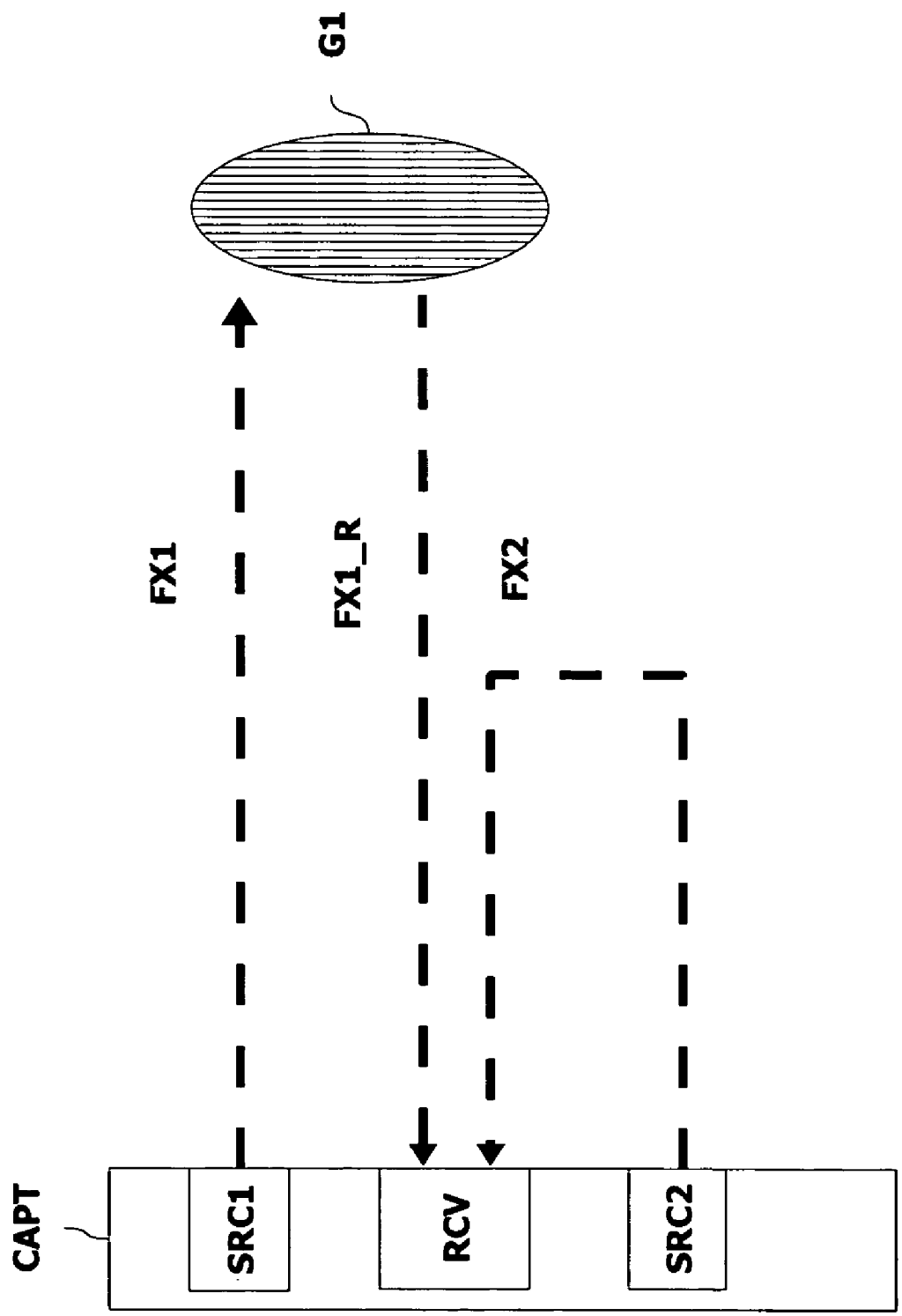
FIG. 3 is a diagram showing in particular a beam of light being emitted which is reflected by an obstacle according to the method in FIG. 1.

FIG. 3 shows a beam FX1 emitted from a source SRC1, the resulting reflected beam FX1_R is received by receiver RCV. FIG. 3 also shows a reference beam FX2, the usefulness of which is explained below.

In a second step (2), one or more detection signals SD are generated as a function of a combination of the reflected beam of light FX1_R in the event of an obstacle O and a reference beam FX2.

Observing a phenomenon which affects visibility such as a spray of water G1 shows that the drops of water which make it up are extremely heterogeneous, as a result of aerodynamic and hydrodynamic turbulence. This heterogeneity is unstable over time, and varies complicatedly as a function of the vehicle's speed and ambient factors (depth of layer of water on the road, type of surfacing used, etc.). The speed with which the drops of water change is slow compared to the response time of a sensor CAPT. It is therefore possible using the sensor CAPT (described further below) to observe a variation in signals representing changes in the drops of water. These signals are the detection signals SD.

Detection signals SD are generated as follows.

A second beam of light FX2 is emitted by a second emitting source SCR2, known as the "compensator", and sent directly to the input of receiver RCV without being reflected by a passing obstacle. The second beam FX2 is of the same type as the first beam FX1, i.e. infra-red.

Reflected beam FX1_R and reference beam FX2 are combined. In a non-limitative embodiment, this combination is based on summing these two signals and a phase shift and amplitude shift between these two signals to give a zero signal. Detection signals SD are representative of the phase shift and amplitude shift. This gives a distance detection signal SD and a reflectivity detection signal SD.

As will be seen below, these detection signals SD can be used in particular to:
a) measure a distance D at which there is a "solid" obstacle behind vehicle V1 and measure its reflectivity;
b) determine the presence of a "soft" obstacle, such as drops of water (coming from a wet road, with or without rain), and hence to detect the presence of one or more sprays of water; and
c) determine the presence of a "soft" obstacle with the presence of a "solid" obstacle such as a following vehicle V2.

Non-limitative examples of detection signals SD are shown in FIGS. 4-7, in which the abscissa represents seconds and the ordinate Volts corresponding to the output from sensor CAPT.

FIG. 4 shows a distance detection signal SD (corresponding to the phase shift mentioned above) of 5 V (default value of sensor CAPT), as there is no disturbing function G1 or "solid" obstacle.

In the first case (a), if the "solid" obstacle is a following vehicle, for example, reflected beam FX1_R has been reflected off the following vehicle V2. It has taken a certain time to be reflected.

This time is reflected in the phase shift (also called "flight time") observed between reflected beam FX1_R and reference beam FX2 which has not been reflected. This time can be used to define the distance D at which the following vehicle V2 is located. Detection signal SD is a continuous straight line.

In the second case (b), if the obstacle is a "soft" obstacle such as drops of water G1, reflected beam FX1_R has been reflected by the drops of water G1. It has also taken a certain time to be reflected. This time is reflected in the phase shift observed between reflected beam FX1_R and reference beam FX2 which was not reflected. This time can be used to determine the distance to the first drop of water (start of spray of water), and hence to determine where the first spray of water starts, the closest to vehicle V1. The continuous signal component SD can be used to observe this distance.

Given, moreover, that the beam is reflected FX1_R from different drops of water and that these drops of water are changing over time (moving), if we observe detection signal SD over a preset time T, we can see that this detection signal is modulated. The variable component of detection signal SD can therefore be used to see this modulation and determine the presence of a spray of water G1, as can be seen in FIGS. 6 and 7.

In the third case (c), where the obstacle is composed of a solid obstacle and a "soft" obstacle, reflected beam FX1_R has been reflected by both water drops G1 and the solid obstacle. The resulting detection signal SD is a combination of information on the distance of the "solid" obstacle and the distance of the "soft" obstacle, and cannot therefore be considered as a reliable measure of the distance of the "solid" obstacle or as a reliable measure of the distance of the "soft" obstacle.

It will be noted that the fact of determining the distance D of an obstacle O by referring to the time emanating from a phase shift between two signals and obtaining a distance accordingly is well known to the average expert, and so will not be described in detail below.

In a third step 3), the modulation of one or more generated detection signals SD is compared with reference data IR.

In a non-limitative embodiment, reference data IR is a modulation threshold.

In a non-limitative embodiment, this modulation threshold is an amplitude modulation threshold. So comparing the amplitude modulation of the detection signal (corresponding to a peak to peak value of the amplitude of the signal oscillations) and this modulation threshold is easily done, as the amplitude modulation of a detection signal SD can be read directly from the signal itself without any particular prior processing. In a non-limitative embodiment, this voltage threshold SU is set at 50 mV. Above this modulation threshold SU, we conclude that there is an interfering phenomenon G1 at the rear of vehicle V1. This modulation threshold can be used to distinguish between a spray of water being present which affects visibility and no spray of water being present, the atmosphere being dry or humid but not affecting visibility.

The cases below are shown in FIGS. 4 to 7. We take as a non-limitative example a distance detection signal SD (corresponding to the phase shift) and reference data IR corresponding to an amplitude modulation threshold.

No Interference Phenomenon G1

If detection signal SD is continuous (or modulated at less than threshold SU), we may conclude there is no spray of water as in FIGS. 4 and 5 and hence no phenomenon affecting visibility.

No Solid Obstacle

If, moreover, the amplitude Vv of detection signal SD is equal to an initial voltage V1 (in this case 5 V), we may conclude that there is no solid obstacle O as shown in FIG. 4.

Solid Obstacle

If, on the other hand, its amplitude Vv is less than the initial voltage V1 (in this case 5V), we may conclude that there is a solid obstacle O and that it is at a certain distance D, depending on the voltage observed, as shown in FIG. 5. As may be seen in this FIG. 5, the average amplitude observed is 4 V on average. In a non-limitative example, 1 V corresponds to one meter. We therefore have a solid obstacle O, such as a following vehicle V2, four meters behind vehicle V1.

In the example shown, a slight modulation may also be observed in signal SD. This modulation is below the preset modulation threshold SU of 50 mV (in the non-limitative example used). We are therefore in the presence of a humid atmosphere, but without any phenomena affecting visibility G1. It will be noted that, in a dry atmosphere, detection signal SD will not be modulated at all, but will be a continuous straight line.

Presence of Interference Phenomenon

If detection signal SD is modulated and the peak to peak value Acc of its modulation exceeds preset modulation threshold SU, we may conclude there are drops of water (with or without a solid obstacle as in FIGS. 6 and 7 respectively) and hence a phenomenon affecting visibility G1.

As was described above, the continuous component of this signal represents the distance to the first drop of water behind vehicle V1. The variable component represents the amplitude modulation of detection signal SD.

What is explained above on comparing with reference data IR may, of course, also be applied to a reflectivity detection signal SD (corresponding to an amplitude shift).

Another embodiment may also combine comparing reference data IR with a distance detection signal SD and comparing reference data IR with a reflectivity detection signal SD.

From observing the modulation of one or more detection signals SD, we can detect the presence of a phenomenon G1 affecting visibility such as a spray of water at the rear of vehicle V1. The greater the modulation, the more turbulence there is at the rear of vehicle V1 and so the greater the interference phenomenon G1. Vehicle V1's rear lights are therefore switched on or increased in brightness accordingly (or are switched on) so a following vehicle V" can see the rear lights of vehicle V1 properly.

In a fourth step 4), once an interference phenomenon G1 is detected, sufficient processing CD in real time can be carried out in vehicle V1.

In the non-limitative examples, this may involve:

increasing the intensity of the rear lights of vehicle V automatically as a function of indications of the presence of an interference phenomenon G1. One will also take account of the presence of an obstacle (increasing the intensity of the lights without dazzling the driver of following vehicle V2); or sending an alarm signal to the driver of vehicle V1 so that he switches the rear lights on and/or makes them brighter himself to provide more light; or switching the rear lights on then regulating their intensity if necessary.

It will be noted that this fourth step is carried out as one detects the presence of an interference phenomenon G1 using the method described above.

Sufficient processing CD such as by adjusting the lighting level of the rear lights automatically is thus performed in real time, as it is made each time an interference phenomenon is detected.

Thanks to the method described above, it is possible to detect:

the presence of an interference phenomenon G1; and the presence of a solid obstacle.

The information that there is a solid obstacle present, such as a following vehicle V2, may be used to manage the intensity of the rear indicators optimally. The intensity of the rear lights may be regulated as a function of whether there is a following vehicle close behind or not (to avoid dazzling). This makes for more safety for the following vehicle. It will be noted that, at the rear of the vehicle, the intensity of the parking lights, for example, is characterized by a number of standard points. According to a European standard, ECE R7, for example, the intensity of these points varies from 0.05 cd to 4 cd at least, depending on the points. The maximum permitted is 12 cd for a single light and 17 cd for a set of lights. If drops of water are detected, therefore, the intensity of the lights is increased, but if drops of water and a vehicle following closely behind are detected, the intensity of the lights is increased accordingly (i.e. less than if that vehicle were not there, to avoid being dazzling and less than in the presence of a vehicle at a distance).

Figure 8:
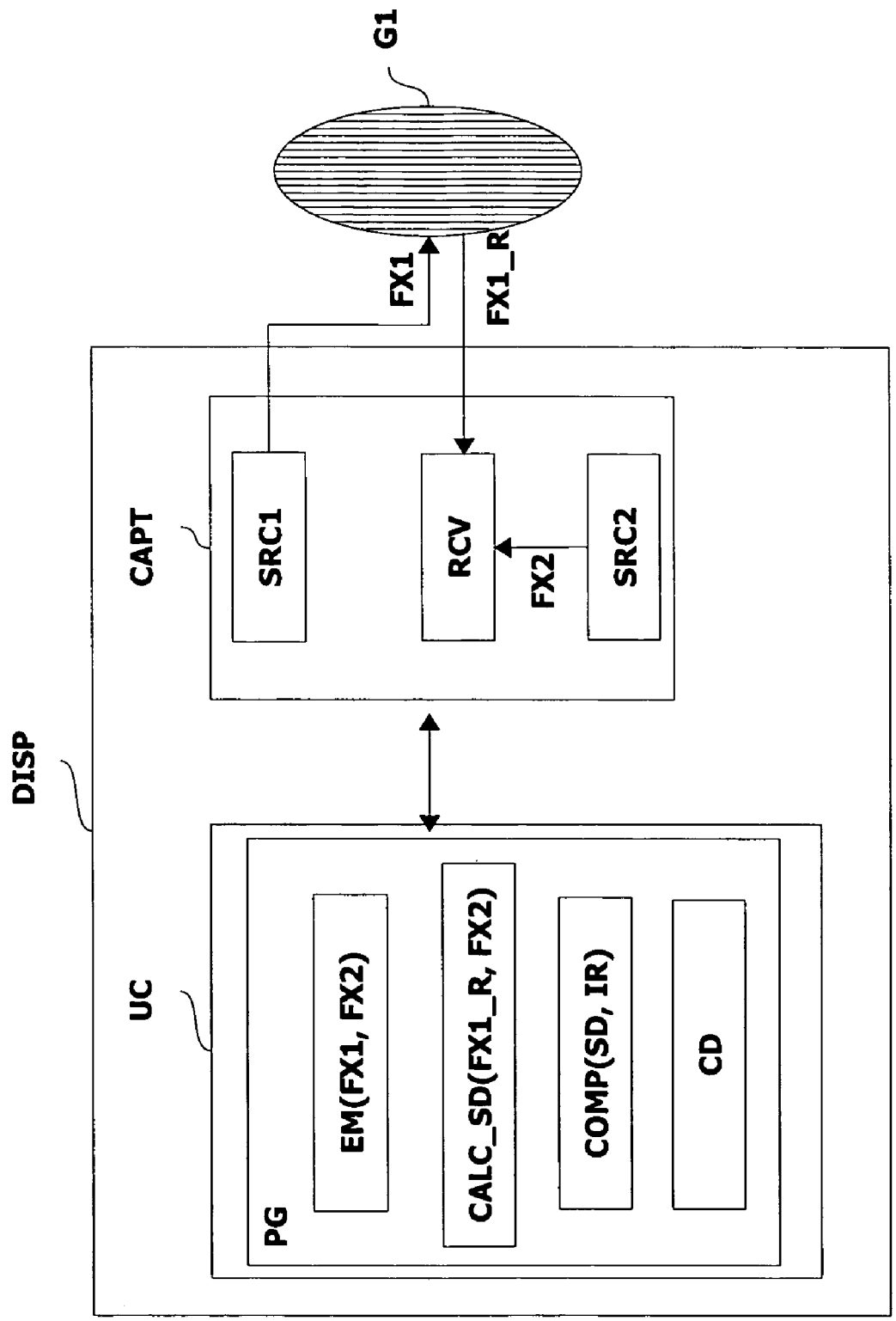
FIG. 8 is a diagram of the detection device enabling the method to be used as in FIG. 1.

The method in the invention is implemented by a detection device DISP as shown in FIG. 8.

This device DISP comprises in particular:

a light source SRC1 emitting a beam of light FX1 to illuminate at the rear of vehicle V1, that beam of light being capable of being reflected by an obstacle O; and a control unit UC for:

generating one or more detection signals SD as a function of a combination of reflected light beam FX1_R if there is an obstacle and a reference beam FX2; and comparing the modulation of one or more detection signals SD with reference data IR.

Device DISP also comprises:

a second light source SRC2 emitting a reference beam FX2;

a receiver RCV for receiving:

reflected beam of light FX1_R resulting from beam of light FX1 being reflected by an obstacle O, and reference beam of light FX2 sent directly to its input (without being reflected by an obstacle O).

The first light source SRC1, second light source SRC2 and receiver RCV together form a sensor CAPT.

Control unit UC can also be used to:

control the first light source SRC1;

control the second light source SRC2;

control receiver RCV;

control (switch lights on/increase their intensity automatically) or execute (send an alarm signal) adequate processing CD; and make comparisons between one or more detection signals SD and reference data IR.

The components of device DISP are described in detail below.

The First Light Source SRC1 ("Emitting Source").

Light source SRC1 is an LED type diode. In other non-limitative embodiments, there may be laser diodes, OLEDs, halogen lights with light foci, etc., any source capable of emitting a beam of light FX1 as described above. It will be recalled that a diode converts electric current to light photons.

This source makes it possible to emit beam of light FX1, that is, it emits pulses of light at a certain frequency.

Source SRC1 is also chosen to emit a beam FX1 of a given range. In a non-limitative example, we will take a range of between five and 20 meters, to be able to be certain of detecting a spray of water at the rear of the vehicle, followed by a following vehicle or not.

In a non-limitative embodiment, it makes it possible to emit a beam at a frequency between 200 and 500 kHz. This makes it possible to use low-cost standard light sources.

In a non-limitative example, source SRC1 is located in one of the rear lights of vehicle V, on account of the protection provided by the glass of the light, or on the rear of the vehicle (close to the vehicle registration number light or tailgate, for example), as these positions can be used to assess the presence of an interference phenomenon G1 produced by the rear wheels. Because of its size (of the order of $cm^3$), infra-red light source SRC1 can in fact be easily integrated in a vehicle's rear light. There is often enough space at the back of a light to take such a device, moreover.

Receiver RCV

In a non-limitative embodiment, the receiver is a photodiode. The receiver depends on the wavelength of the beam of light FX used.

In another non-limitative example, the receiver may be a InGaAS receiver if the beam of light FX emitted is of InGaAS wavelength. This makes it possible to emit in a frequency band which is less harmful to the human eye than infra-red and increase the optical power to detect further off.

The interest in using a photodiode is to obtain a low-cost sensor CAPT. It will be recalled that a photodiode converts the photons received as light to electric current.

This receiver can be used to:

receive reflected light beam FX1_R, and receive reference beam FX2.

Receiver RCV is placed in the return path of the pulse of light sent (or, again, the light emitted). It is therefore located in a position where it is illuminated by reflected beam FX1_R.

In a non-limitative embodiment, receiver RCV is located close to emitting source SRC1 to give more return signal detected of beam of light FX1. This also makes it possible to have a better gain in efficiency and simplicity of management of the receiver electronics.

It will be recalled that reflected beam of light FX1_R is composed of pulses which have been reflected by any "solid" obstacle (vehicle, wall, pedestrian, pavement etc.) and/or not "solid"="soft" (water, fog etc.) and which has been returned in the direction of emitter SRC1 and receiver RCV, distorted by the obstacle (absorption, shape of the obstacle etc.) and put out of phase.

The Second Light Source SRC2 ("Reference Source").

The second light source SRC2 is an LED-type "reference" diode. In other non-limitative embodiments, there might be laser diodes, OLEDs, halogen lamps with light concentrators etc., any source capable of emitting a reference beam of light FX2 as described above.

This source can be used to emit reference beam of light FX2, which is of the same type as beam of light FX1 when first emitted (infra-red, same frequency).

Reference light source SRC2 illuminates receiver RCV continuously. It thus sends sensor CAPT the same pulses of light as the first light source SRC1, but sends them directly (that is, without passing via an obstacle) to the receiver.

In a non-limitative embodiment, it is located not far from receiver RCV to simplify the light path to be traversed.

Sensor CAPT

These three components SRC1, SRC2 and RCV thus form a sensor CAPT. This sensor CAPT does not take up much space (smaller than a pack of cigarettes) if these three components are put side by side.

It will be noted that it is also possible to have a single component acting as emitter and receiver. A diode, for example (i.e. emitting) can be made to work as a photodiode (i.e. receiving), alternating these functions in turn, but this solution is more complicated to manage and increases the cost of the sensor CAPT.

Moreover, as was described above, sensor CAPT is selected such that its response time (also called "time resolution") is less than the speed at which drops of water change, making it possible to observe a variation in the signal representing changes in drops of water and hence modulating a detection signal SD.

It will be noted that the rate of change of these water drops is the characteristic period of motion of those drops behind the vehicle (the water drops rising and falling at a certain speed).

Sensor CAPT is capable of distinguishing two pulses of light.

Control Unit UC

This can be used to control the emission of reference source SRC2 so as to vary reference beam FX2 (particularly via phase and amplitude shifts) relative to reflected beam of light FX1_R to give a zero signal when summated with reflected beam of light FX1_R. This unit UC can be used to measure phase and amplitude shift and hence to obtain the detection signals SD described above (distance and reflectivity). Such a unit UC enabling signals to be shifted is known to the average expert, and is simple to use, as it enables two signals to be adjusted (reference and emitted) such as to cancel the two beams FX1_R and FX2 by making just one signal shift as described above.

No very short measure of time less than 100 ns (equivalent approximately to the flight time of a pulse of light) is necessary by assessing the flight time of a pulse of light between its emitter and receiver. So no high-quality electronics are required (equivalent to military hardware) which would be difficult to reconcile with the costs allowed in an automobile.

It will be noted that, in a non-limitative embodiment, the sensor CAPT and hence detection device DISP cuts in once the vehicle exceeds a given threshold speed SV described above. Below this threshold, in fact, no spray of water is generated; or, if it is generated, it is not a nuisance at low speeds. This also makes it possible to consume less current and hence less energy.

It will be noted that the detection method as presented above may be implemented using a micro-programmed "software" device, hard-wired logic or, again, electronic components "hardware".

Thus, detection device DISP may have a computer program PG having one or more sequences of instructions capable of being executed by a data processing unit such as a microprocessor or a processing unit of a micro-controller, an ASIC, a computer etc., executing the sequences of instructions making it possible to use the method above.

Such a computer program PG may be written in a non-volatile writeable ROM type memory or in non-volatile rewritable ROM type memory or in non-volatile rewritable EEPROM or FLASH type memory, for example. The computer program PG may be written in the memory at the factory, or be loaded or remote loaded in memory. The instruction sequences may be machine instruction sequences or control language sequences which the processing unit interprets when it executes them.

In the non-limitative example in FIG. 8, computer program PG is written in a memory of control unit UC.

The description of the method is not, of course, limited to the embodiments or examples described. In a non-limitative embodiment, for example, it would also be possible, in the third step (3) to compare the modulation of one or more detection signals SD with reference data IR which is a frequency modulation threshold, thus taking account of the frequency modulation of a detection signal SD.

Another embodiment might equally, conceivably, combine such a comparison (with a frequency modulation threshold) with an amplitude modulation threshold as described previously.

The advantages of the invention are thus, in particular, as follows:

it can be used to detect one or more sprays of water and switch on and/or increase the intensity of the rear lights accordingly;

it can be used to give a low-cost sensor (in particular by using the photodiode and because the method of detection is simple);

this solution is easy to implement, because of the combination (summation and phase and amplitude shift) which is easy to make;

the phase shift and amplitude shift are simple to use, so a standard frequency (200-500 kHz) sensor can be used;

it can be used to determine whether an obstacle O at the rear of vehicle V1 is a phenomenon which interferes with visibility generated by vehicle V1;

it can be used to detect a humid atmosphere which does not interfere with visibility thanks to the voltage threshold SU;

it makes it possible to ignore meteorological constraints (very short flight times of pulses of light): so no electronics or complex control unit is required. Standard components only can be used;

it makes it possible to use a device which takes up little space, thanks to being simple to implement;

it can be used to determine if an obstacle at the rear of a vehicle is a phenomenon affecting visibility;

it is not necessary to analyze how the form of a pulse of light is distorted to evaluate the conjugation of the back scatter on a "soft" obstacle and reflection on a "solid" obstacle. This avoids using expensive components, optical and electronic particularly.

While the method herein described, and the form of apparatus for carrying this method into effect, constitute preferred embodiments of this invention, it is to be understood that the invention is not limited to this precise method and form of apparatus, and that changes may be made in either without departing from the scope of the invention, which is defined in the appended claims.

What is claimed is:

1. A method of detection for detecting a phenomenon affecting visibility generated by an automotive vehicle, said method comprising the steps of:
    emitting a first beam of light, which beam of light can be reflected by an obstacle to provide a reflected beam of light;
    emitting a second reference beam of light using a second emitting source;
    receiving on a receiver the reflected beam of light resulting from the first beam of light being reflected by an obstacle, and said second reference beam of light sent directly to the receiver input;
    generating one or more detection signals as a function of a combination of said reflected beam of light if there is an obstacle and said second reference beam of light; and
    comparing the modulation of one or more detection signals generated with reference data;
    wherein said first beam of light and said second reference beam of light are infra-red beams, and said first beam of light is directed rearward of the vehicle;
    wherein said combination of the reflected beam of light and said second reference beam of light comprises a summation of said first beam of light and said second reference beam of light;
    said preceding method steps being conducted during movement of the vehicle and said receiver being located on the vehicle such that it directs said first beam of light rearward.

2. The method of detection according to claim 1, wherein said combination further comprises a phase shift and an amplitude shift of those two beams.

3. The method of detection according to claim 2, wherein a detection signal corresponds to a phase shift between the reflected beam of light and said second reference beam of light.

4. The method of detection according to claim 2, wherein the reference data is a preset modulation threshold.

5. The method of detection according to claim 1, wherein a detection signal corresponds to a phase shift between said reflected beam of light and said second reference beam of light.

6. The method of detection according to claim 5, wherein the reference data is a preset modulation threshold.

7. The method of detection according to claim 1, wherein the reference data is a preset modulation threshold.

8. The method of detection according to claim 1, wherein the reference data is an amplitude modulation threshold.

9. The method of detection according to claim 1, wherein the phenomenon affecting visibility consists of a spray of water generated by the wheels of vehicle.

10. A method of detection for detecting a phenomenon affecting visibility generated by an automotive vehicle comprising the steps of:
    emitting a first beam of light, which beam of light can be reflected by an obstacle to provide a reflected beam of light;
    emitting a second reference beam of light using a second emitting source;
    receiving on a receiver the reflected beam of light resulting from said first beam of light being reflected by an obstacle, and said second reference beam of light sent directly to the receiver input;
    generating one or more detection signals as a function of a combination of the reflected beam of light if there is an obstacle and said second reference beam of light; and
    comparing the modulation of one or more detection signals generated with reference data;
    wherein said first beam of light and said second reference beam of light are infra-red beams, and they are directed towards the rear of a vehicle;
    wherein emitting said first beam of light is triggered from a preset speed threshold of the vehicle.

11. A detection device for detecting a phenomenon affecting visibility generated by an automotive vehicle, comprising:
    a first emitting source for emitting a first beam of light to illuminate at a rear of the vehicle, which beam of light may be reflected by an obstacle to provide a reflected beam of light;
    a second light source emitting a second reference beam of light;
    a receiver for receiving:
        said reflected beam of light resulting from said first beam of light being reflected by an obstacle, and
        said second reference beam of light sent directly to its input, and a control unit for:
        generating one or more detection signals as a function of the combination of the reflected beam of light in the event of an obstacle and said second reference beam of light; and
        comparing the modulation of one or more detection signals generated using reference data;
    each of said first emitting source, said second light source, said receiver and said control unit being located on the vehicle;
    wherein said first beam of light and said second reference beam of light are infra-red beams, and that they are directed rearward or towards a rear of the vehicle;
    wherein said combination of the reflected beam of light and said second reference beam of light comprises a summation of said first beam of light and said second reference beam of light.

12. A detection device for detecting a phenomenon affecting visibility generated by an automotive vehicle comprising:
    a first emitting source for emitting a first beam of light to illuminate at a rear of the vehicle, which beam of light may be reflected by an obstacle to provide a reflected beam of light;
    a second light source emitting a second reference beam of light;
    a receiver for receiving:
        said reflected beam of light resulting from said first beam of light being reflected by an obstacle; and
        said second reference beam of light sent directly to its input, and a control unit for:
generating one or more detection signals as a function of the combination of the reflected beam of light in the event of an obstacle and said second reference beam of light; and
comparing the modulation of one or more detection signals generated using reference data;
wherein said first beam of light and said second reference beam of light are infra-red beams, and that they are directed towards the rear of the vehicle;
wherein the detection device is active from a preset speed threshold of vehicle.

13. A computer program product comprising one or more sequences of instructions which can be executed by a data processing unit, the sequences of instructions enabling the method to be implemented according to the following steps:
emitting a first beam of light, which said first beam of light can be reflected by an obstacle to provide a reflected beam of light;
emitting a second reference beam of light using a second emitting source;
receiving on a receiver the reflected beam of light resulting from the first beam of light being reflected by an obstacle, and the second reference beam of light sent directly to the receiver input;
generating one or more detection signals as a function of a combination of said reflected beam of light if there is an obstacle and a reference beam; and
comparing the modulation of said one or more detection signals generated with reference data;
wherein said first beam of light and said second reference beam of light are infra-red beams, said first beam of light is directed rearward or toward a rear of the vehicle;
wherein said combination of the reflected beam of light and said second reference beam of light comprises a summation of said first beam of light and said second reference beam of light.

14. A method of detection for detecting a phenomenon affecting visibility generated by an automotive vehicle comprising the steps of:
emitting a first beam of light, which beam of light can be reflected by an obstacle to provide a reflected beam of light;
emitting a second reference beam of light using a second emitting source;
receiving on a receiver said reflected beam of light resulting from said first beam of light being reflected by said obstacle, and said second reference beam of light sent directly to the receiver input;
generating one or more detection signals as a function of a combination of the reflected beam of light if there is an obstacle and said second reference beam of light; and
comparing the modulation of one or more detection signals generated with reference data;
wherein said first beam of light and said second reference beam of light are infra-red beams, and they are directed towards the rear of the vehicle;
wherein the combination consists of summating the two beams, a phase shift and an amplitude shift of those two beams;
wherein emitting the beam of light is triggered from a preset speed threshold of the vehicle.

15. A method of detection for detecting a phenomenon affecting visibility generated by an automotive vehicle comprising the steps of:
emitting a first beam of light, which beam of light can be reflected by an obstacle to provide a reflected beam of light;
emitting a second reference beam of light using a second emitting source;
receiving on a receiver the reflected beam of light resulting from the first beam of light being reflected by an obstacle, and the second reference beam of light sent directly to the receiver input;
generating one or more detection signals as a function of a combination of the reflected beam of light if there is an obstacle and said second reference beam of light: and
comparing the modulation of one or more detection signals generated with reference data:
wherein said first beam of light and said second reference beam of light are infra-red beams, and they are directed towards the rear of the vehicle:
wherein the reference data is a preset modulation threshold:
wherein emitting the beam of light is triggered from a preset speed threshold of the vehicle.

16. The method of detection according to claim 15, wherein the phenomenon affecting visibility consists of a spray of water generated by the wheels of said vehicle.

17. The method of detection according to claim 15, wherein the phenomenon affecting visibility consists of a spray of water generated by the wheels of said vehicle.

18. A detection device for detecting a phenomenon affecting visibility generated by an automotive vehicle comprising:
a first emitting source for emitting a first beam of light to illuminate at a rear of the vehicle, which beam of light may be reflected by an obstacle to provide a reflected beam of light;
a second light source emitting a second reference beam of light;
a receiver for receiving:
said reflected beam of light resulting from said first beam of light being reflected by an obstacle; and
said second reference beam of light sent directly to its input; and
a control unit for:
generating one or more detection signals as a function of the combination of the reflected beam of light in the event of an obstacle and said second reference beam of light; and
comparing the modulation of one or more detection signals generated using reference data;
wherein said first beam of light and said second reference beam of light are infra-red beams, and that they are directed towards the rear of the vehicle;
wherein an intensity of light from rear lights on said vehicle is adjusted in response to said detection.

* * * * *